United States Patent [19]

Beauquey et al.

[11] Patent Number: 5,308,551
[45] Date of Patent: May 3, 1994

[54] WASHING COMPOSITIONS BASED ON SILICONES AND PROCESS OF APPLICATION

[75] Inventors: Bernard Beauquey, Clichy; Claude Dubief, Le Chesnay, both of France

[73] Assignee: L'Oreal, Paris, France

[21] Appl. No.: 752,360

[22] Filed: Sep. 3, 1991

[30] Foreign Application Priority Data

Aug. 31, 1990 [FR] France .................. 90 10894

[51] Int. Cl.$^5$ .................. C11D 1/04; C11D 1/755
[52] U.S. Cl. .................. 252/548; 252/174.15; 252/DIG. 13
[58] Field of Search .......... 252/548, 174.15, DIG. 13

[56] References Cited

U.S. PATENT DOCUMENTS

| | | | |
|---|---|---|---|
| 4,559,227 | 12/1985 | Chandra et al. | 424/70 |
| 4,675,125 | 6/1987 | Sturwold | 252/174.15 |
| 4,714,479 | 12/1987 | Wilsberg | 252/174.15 |
| 4,820,308 | 4/1989 | Madrange et al. | 252/DIG. 13 |
| 5,063,044 | 11/1991 | Kohl et al. | 252/DIG. 13 |
| 5,130,056 | 7/1992 | Jacobson et al. | 252/DIG. 13 |

FOREIGN PATENT DOCUMENTS

| | | |
|---|---|---|
| 141593 | 5/1985 | European Pat. Off. . |
| 158174 | 10/1985 | European Pat. Off. . |
| 323594 | 7/1989 | European Pat. Off. . |

*Primary Examiner*—Asok Pal
*Attorney, Agent, or Firm*—Jacobson, Price, Holman & Stern

[57] ABSTRACT

The invention relates to a composition for washing and conditioning keratinous substances, in particular hair and the skin, characterised in that it contains in an aqueous medium
- at least one detergent surface-active agent,
- at least one insoluble silicone,
- at least one myristate of a $C_2$–$C_4$ polhydric alcohol.
- at least one ($C_1$–$C_4$)alkanolamide alkyl ether and/or a $C_8$–$C_{16}$ fatty acid ($C_1$–$C_4$)alkanolamide.

25 Claims, No Drawings

WASHING COMPOSITIONS BASED ON SILICONES AND PROCESS OF APPLICATION

The present invention relates to compositions for washing and conditioning keratinous substances, in particular hair and/or the skin, and comprising, in an aqueous medium, at least one silicone which is insoluble in the presence of surface-active agents, and to the washing processes making use of these compositions.

Compositions for washing keratinous substances, especially shampoos, are well known in the state of the art.

It has already been proposed to employ silicones in such compositions, especially insoluble silicones imparting to the keratinous substances treated, and in particular to hair, advantageous conditioning properties such as sheen softness and gentle disentangling.

Bearing in mind the insoluble nature of these silicones in the aqueous media usually employed in shampoos, attempts are made to keep the silicones in a dispersed form while retaining the detergent and foaming properties of the composition and without lowering the viscosity. These compositions must also endow the hair with the required properties of softness, sheen and disentangling.

The Applicant has found that, surprisingly, it is possible to prepare washing compositions which are particularly stable with time and which have good detergency properties while endowing the hair with sheen, softness and ease of combing, by employing, in addition to the detergent surface-active agents, a mixture of two surface-active agents chosen from (a) a myristate of a $C_2$–$C_4$ polyhydric alcohol, and (b) an alkyl ether of a ($C_1$–$C_4$) alkanolamide and/or a ($C_1$–$C_4$) alkanolamide derived $C_8$–$C_{16}$ from a fatty acid.

The Applicant has found in particular that these two surface-active agents, when employed by themselves in the presence of a detergent surface-active agent and of an insoluble silicone, do not make it possible to obtain stable compositions in the form of a suspension, but that their combination makes it possible at the same time to solve the problem of stability of the compositions with time, to convey the silicone onto the hair and to endow the latter with good softness, disentangling and sheen properties. These compositions also have excellent foaming and washing properties without being difficult to rinse off.

Furthermore, these compositions offer the advantage of being capable of being produced without difficulty with the aid of conventionally employed processes and equipment.

The subject of the invention is therefore a washing composition containing at least one insoluble silicone, a detergent surface-active agent and the combination of two particular surface-active agents defined below.

Another subject of the invention consists of the washing process making use of these compositions.

Other subjects of the invention will appear on reading the description and the examples which follow.

The composition in accordance with the invention is essentially characterised in that it contains, in an aqueous medium
- at least one surface-active agent which has detergent properties,
- at least one insoluble silicone,
- at least one myristate of a $C_2$–$C_4$ polyhydric alcohol,
- at least one ($C_1$–$C_4$)alkanolamide alkyl ether and/or a ($C_1$–$C_4$)alkanolamide derived from a $C_8$–$C_{16}$ fatty acid.

The various components of the washing composition in accordance with the invention are preferably employed in the following proportions, these proportions being expressed by weight of the total weight of the composition:
- 5 to 50% of the surface-active agent which has detergent properties,
- 0.1 to 20% of at least one insoluble silicone,
- 1 to 8% of myristate of $C_2$–$C_4$ polyhydric alcohol,
- 0.5 to 8% of alkanolamide alkyl ether and/or of $C_8$–$C_{16}$ fatty acid ($C_1$–$C_4$)alkanolamide.

The detergent surface-active agents are chosen from anionic, nonionic, amphoteric and zwitterionic surface-active agents or their mixtures.

Among the anionic surface-active agents there may be mentioned more particularly the acylisethionates, the alkyl methyltaurates and the alkali metal, magnesium, ammonium, amine or aminoalcohol salts of the following compounds:
- alkyl sulphates, alkyl ether sulphates, alkylamidoether sulphates, alkylaryl polyether sulphates, monoglyceride sulphates;
- alkylsulphonates, alkylamidesulphonates, alkylarylsulphonates, olefin sulphonates, paraffin sulphonates;
- alkylsulphosuccinates, alkyl ether sulphosuccinates, alkylamidesulphosuccinates;
- alkylsulphosuccinamates;
- alkylsulphoacetates;
- alkyl phosphates, alkyl ether phosphates;
- acylsarcosinates.

The alkyl or acyl radical in these various compounds generally consist of a carbon chain containing from 12 to 20 carbon atoms.

Among the anionic surface-active agents there may also be mentioned:
fatty acid salts such as salts of oleic, ricinoleic, palmitic and stearic acids, of copra oil or hydrogenated copra oil acids, and acyllactylates in which the acyl radical contains from 8 to 20 carbon atoms.

Among the surface-active agents considered to be weakly anionic there may be mentioned:
polyoxyalkylenated carboxylic ether acids corresponding to the formula:

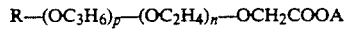

$$R-(OC_3H_6)_p-(OC_2H_4)_n-OCH_2COOA$$

in which R denotes an alkyl radical or a mixture of linear or branched, $C_8$–$C_{22}$ alkyl or alkenyl radicals, a ($C_8$–$C_9$)alkylphenyl radical, or R'CONH—CH$_2$—CH$_2$— radical with R' denoting a $C_{11}$–$C_{21}$, linear or branched alkyl or alkenyl radical;

n is an integer or decimal number between 2 and 24,
p is an integer or decimal number between 0 and 6,
A denotes a hydrogen atom or Na, K, Li, ½ Mg or a monoethanolamine, ammonium or triethanolamine residue.

The nonionic surface-active agents are chosen more particularly from alcohols, alkylphenols and polyethoxylated, polypropoxylated or polyglycerolated fatty acids with a fatty chain containing 8 to 18 carbon atoms. The number of ethylene oxide or propylene oxide groups being between 2 and 50 and the number of glycerol groups being between 2 and 30.

There may also be mentioned the copolymers of ethylene and propylene oxides, condensates of ethylene and propylene oxides with fatty alcohols, polyethoxylated fatty amides preferably containing 2 to 30 moles of ethylene oxide, polyglycerolated fatty amides containing 1 to 5 and preferably 1.5 to 4 glycerol groups, polyethoxylated fatty amines preferably containing 2 to 30 moles of ethylene oxide, oxyethylenated sorbitan fatty acid esters preferably containing 2 to 30 moles of ethylene oxide, sucrose fatty acid esters, polyethylene glycol fatty acid esters, phosphoric triesters, and amine oxides such as alkylamine or N-acylamidopropylmorpholine oxides.

The more particularly preferred amphoteric or zwitterionic surface-active agents are:

- derivatives of aliphatic secondary or tertiary amines in which the aliphatic radical is a linear or branched chain containing 8 to 18 carbon atoms and which contains at least one carboxylic, sulphonate, sulphate, phosphate or phosphonate hydrosolubilising anionic group;
- ($C_8$-$C_{20}$)alkylbetaines, sulphobetaines, ($C_8$-$C_{20}$)-alkylamido ($C_1$-$C_6$)alkylbetaines or ($C_8$-$C_{20}$) alkylamido ($C_1$-$C_6$)-alkylsulphobetaines.

Among these compounds there may be mentioned the products sold under the name "Miranol", as described in U.S. Pat. Nos. 2,528,378 and 2,781,354 and classified in the CTFA Dictionary, 3rd Edition, 1982, under the name of Amphocarboxyglycinates and Amphocarboxypropionates.

The alkylbetaines are preferably chosen from ($C_{10}$-$C_{20}$) alkylbetaines.

The silicones employed in accordance with the invention are polyorganosiloxanes which are insoluble in the aqueous medium and which can be in the form of oils, waxes, resins or gums.

Nonvolatile silicones are preferably employed, and more particularly polyalkylsiloxanes, polyarylsiloxanes, polyalkylarylsiloxanes, silicone gums and resins, polyorganosiloxanes modified with organofunctional groups and their mixtures.

These silicones are chosen more particularly from polyalkylsiloxanes, among which there may be mentioned linear polydimethylsiloxanes containing trimethylsilyl end groups which have a viscosity of $5 \times 10^{-6}$ to 2.5 at $m^2/s$ at 25° C. and preferably $1 \times 10^{-5}$ to 1 $m^2/s$.

The following commercial products may be mentioned among these polyalkylsiloxanes, no limitation being implied:

- the Silbione oils of Series 47 and 70 047 marketed by Rhone-Poulenc, such as the 47 V 500 000 and 47 V 300 oils;
- the Series 200 oils from Dow Corning;
- the Viscasil oils from General Electric and some Series SF oils (SF 96, SF 18) from General Electric.

Mention may also be made of the linear polydimethylsiloxanes containing dimethylsilanol end groups, such as the Series 48 oils from Rhone-Poulenc.

In this class of polyalkylsiloxanes it is also possible to mention the products sold under the names "Abil Wax 9800 and 9801" by Goldschmidt, which are poly($C_1$-$C_{20}$) alkylsiloxanes.

The polyalkylarylsiloxanes are chosen from linear and/or branched polydimethylmethylphenylsiloxanes and polydimethyldiphenylsiloxanes with a viscosity of $1 \times 10^{-5}$ to $5 \times 10^{-2}$ $m^2/s$ at 25° C.

Among these polyalkylarylsiloxanes there may be mentioned by way of example the products marketed under the following names:

- the Silbione oils of Series 70 641 from Rhone-Poulenc;
- the oils of the Rhodorsil 70 633 and 763 Series from Rhone-Poulenc;
- the oil DC 556 Cosmetic Grad Fluid from Dow Corning;
- the silicones of Series PK from Bayer, such as the product PK20;
- the silicones of the Series PN and PH from Bayer, such as the products PN 1000 and PH 1000;
- some oils of the SF Series from General Electric, such as SF 1023, SF 1154, SF 1250 and SF 1265.

The silicone gums which can be employed in accordance with the invention are especially polydiorganosiloxanes which have high molecular masses of between 200,000 and 1,000,000, employed by themselves or as a mixture in a solvent. This solvent may be chosen from volatile silicones, polydimethylsiloxane oils (PDMS), polyphenylmethylsiloxane oils (PPMS), isoparaffins, methylene chloride, pentane, dodecane, tridecane, tetradecane and mixtures thereof.

The following products may be mentioned more particularly:
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Other products which can be employed in accordance with the invention are mixtures such as:

- the mixtures made up of a polydimethylsiloxane hydroxylated at a chain end (called dimethiconol according to the nomenclature of the CTFA Dictionary) and of a cyclic polydimethylsiloxane (called cyclomethicone according to the nomenclature of the CTFA Dictionary), such as the product Q2 1401 sold by Dow Corning;
- the mixtures made up of a polydimethylsiloxane gum with a cyclic silicone such as the product SF 1214 Silicone Fluid from General Electric, this product is an SE 30 gum corresponding to a dimethicone which has a molecular weight of 500,000, solubilised in SF 1202 Silicone Fluid oil corresponding to decamethylcyclopentasiloxane;
- mixtures of two PDMSs of different viscosities, and more particularly of a PDMS gum and of a PDMS oil, such as the products SF 1236 or CF 1241 from General Electric. The product SF 1236 is the mixture of an SE 30 gum defined above which has a viscosity of 20 $m^2/s$ and of an SF 96 oil with a viscosity of 5x Is. This product preferably contains 15% of SE 30 gum and 85% of an SF 96 oil. The product CF 1241 is the mixture of an SE 30 gum (33%) and of an PDMS oil (67%) with a viscosity of $10^{-3}$ $m^2/s$.

The organopolysiloxane resins which can be employed in accordance with the invention are crosslinked siloxane systems containing the units $R_2SiO_{2/2}$, $RSiO_{3/2}$ and $SiO_{4/2}$.

Among these resins, those in which R denotes a $C_1$-$C_6$ lower alkyl radical or a phenyl radical are preferred.

Among these resins there may be mentioned the product sold under the name "Dow Corning 5931" or those sold under the names "Silicone Fluid SS 4230 and SS 42671" by General Electric and which are siloxanes with a dimethyl/trimethylsiloxane structure.

The organomodified silicones which can be employed in accordance with the invention are silicones such as defined above and containing in their structure one or more organofunctional groups attached directly to the siloxane chain or attached by means of a hydrocarbon radical.

Among these silicones there may be mentioned silicones containing:

polyethyleneoxy and/or polypropyleneoxy groups optionally containing alkyl groups, such as the product called dimethicone copolyol sold by Dow Corning under the name DC 1248 and the alkyl ($C_{12}$) methicone copolyol sold by Dow Corning under the name Q2 5200, and Silwet L 722, L 7500, L 77 and L 711 oils from Union Carbide;

substituted or unsubstituted amine groups, such as the products sold under the name GP4 Silicone Fluid and GP 7100 by Genesee or the products sold under the names Q2 8220 and DC 929 by Dow Corning. The substituted amine groups are in particular $C_1$-$C_4$ alkylamino groups;

thiol groups such as the products sold under the names "GP 72 A" and "GP 711" from Genesee;

carboxylate groups, such as the products described in the Chisso Corporation Patent EP 186,507;

alkoxylated groups, such as the product sold under the name "Silicone Copolymer F-755" by SWS Silicones and Abil Wax 2428, 2434 and 2440 by Goldschmidt;

hydroxylated groups, such as polyorganosiloxanes containing a hydroxyalkyl functional group, which are described in French Patent Application FR-A-85 16,334, corresponding to the formula (I):

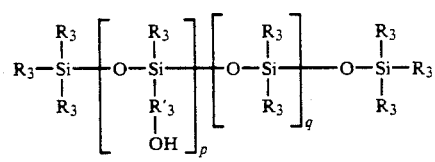

(I)

in which the radicals $R_3$, which are identical or different, are chosen from methyl and phenyl radicals, at least 60 mol % of the radicals $R_3$ denoting methyl; the radical $R'_3$ is a $C_2$-$C_{18}$ divalent hydrocarbon alkylene chain unit, p is between 1 and 30 inclusive, and q is between 1 and 150 inclusive;

acyloxyalkyl groups, such as, for example, the polyorganosiloxanes described in French Patent Application FR-A-2,641,185 and corresponding to the formula (II):

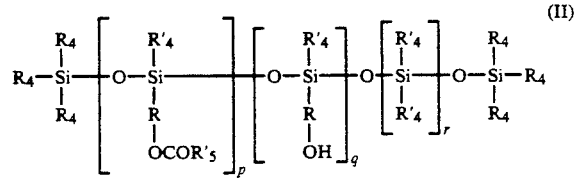

(II)

in which:

$R_4$ denotes a methyl, phenyl, —OCR" or hydroxyl group, with only one of the radicals $R_4$ per silicon atom capable of being OH;

$R'_4$ denotes methyl or phenyl, at least 60 mol % of the total of radicals $R_4$ and $R'_4$ denoting methyl;

$R'_5$ denotes $C_8$-$C_{20}$ alkyl or alkenyl;

R denotes a $C_2$-$C_{18}$, linear or branched divalent hydrocarbon alkylene radical;

r is between 1 and 120 inclusive;

p is between 1 and 30;

q is equal to 0 or is smaller than 0.5 p, p+q being between 1 and 30; it being possible for the polyorganosiloxanes of formula (II) to contain

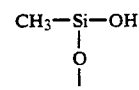

groups in proportions not exceeding 15% of the sum p+q+r;

anionic groups of carboxylic type, such as the alkylcarboxylic groups like those present in the product X-22-3701E from Shin-Etsu; of 2-hydroxyalkylsulphonate type and of 2-hydroxyalkylthiosulphate type, such as the products sold by Goldschmidt under the names "Abil S201" and "Abil S 255".

hydroxyacylamino groups, such as the products described in Application EP-A-0,342,834. Such silicones are sold in particular under the name Q2-8413 by Dow Corning.

It is also possible to employ volatile silicones which have a boiling point of between 60° C. and 260° C.

The volatile silicones are chosen more particularly from:

(i) cyclic silicones containing from 3 to 7 and preferably 4 to 5 silicon atoms. These are, for example, the octamethylcyclotetrasiloxane sold under the name of Volatile Silicone 7207 by Union Carbide or Silbione 70045 V 2 by Rhone Poulenc, the decamethylcyclopentasiloxane sold under the name of Volatile Silicone 7158 by Union Carbide, Silbione 70045 V 5 by Rhone-Poulenc, and their mixtures.

Mention is also made of the cyclocopolymers of the dimethylsiloxane/methylalkylsiloxane type, such as the Silicone Volatile FZ 3109 sold by Union Carbide, in which alkyl denotes $C_8H_{17}$.

It is also possible to mention mixtures of cyclic silicones with organic compounds derived from silicon, such as the mixture of octamethylcyclotetrasiloxane and of tetratrimethylsilylpentaerythritol (50/50) and the mixture of octamethylcyclotetrasiloxane and of 1,1′-oxy(2,2,2′,2′,3,3′-hexatrimethylsilyloxy)bisneopentane;

(ii) linear volatile silicones containing 2 to 9 silicon atoms and possessing a viscosity lower than or equal to $5 \times 10^{-6}$ m²/s at 25° C. These are, for example, the hexamethyldisiloxane sold under the name Silbione 70 041 V 0.65 by Rhone-Poulenc and the decamethyltetrasiloxane sold under the name SH 200 by Toray Silicone. Silicones which are members of this class are also described in the article published in Cosmetics and Toiletries, Vol. 91, Jan. 76, p. 27-32—Todd & Byers "Volatile Silicone fluids for cosmetics".

The washing composition according to the invention preferably contains:

from 1.5 to 5% of myristate of a $C_2$-$C_4$ polyhydric alcohol consisting especially of ethylene glycol, propylene glycol and glycerol.

The myristate of a polyhydric alcohol is a commercial product which consists of at least 95% $C_{14}$.

Ethylene glycol dimyristate is particularly preferred. From 0.5 to 8% of an amide chosen from:
a) ($C_1$-$C_4$) alkanolamide alkyl ethers, the alkyl chain containing from 13 to 15 carbon atoms; the preferred compound is ($C_{13}$-$C_{15}$) alkoxydiethoxymethylmonoethanolamide such as the product sold under the name Aminol A15 by Chem'Y;
b) ($C_1$-$C_4$)alkanolamides of $C_8$-$C_{16}$ fatty acids, such as copra diethanolamide, copra monoethanolamide or copra monoisopropanolamide;

from 1 to 10% by weight of silicone and more particularly from 1 to 4% by weight, relative to the total weight of the composition.

The detergent surface-active agents are in sufficient proportions to impart a detergent nature to the composition, in particular of between 8 and 30% by weight.

In the compositions in accordance with the invention, mixtures of surface-active agents are employed and in particular mixtures of anionic surface-active agents and amphoteric, zwitterionic or nonionic surface-active agents are preferably employed.

An anionic surface-active agent which is preferably employed is chosen from sodium, triethanolamine or ammonium ($C_{12}$-$C_{14}$) alkyl sulphates, sodium($C_{12}$-$C_{14}$)alkyl ether sulphates oxyethylenated with 2.2 moles of ethylene oxide, sodium cocoylisethionate, and sodium ($C_{14}$-$C_{16}$)-$\alpha$-olefin sulphonates and their mixtures with
either an amphoteric surface-active agent such as an amphocarboxyglycinate defined above;
or a zwitterionic surface-active agent such as laurylbetaine sold under the name Dehyton AB 30 in aqueous solution at a concentration of 32% of AS by Henkel.

When the amphoteric or zwitterionic surface-active agents are employed as a mixture with anionic surface-active agents, they represent up to 50% and preferably from 5 to 30% by weight relative to the total weight of the quantity of surface-active agents present in the composition.

When the nonionic surface-active agents are employed as a mixture with anionic surface-active agents, they represent up to 90% and preferably 5 to 50% by weight relative to the total quantity of surface-active agents present in the composition.

The pH of these compositions is generally between 3 and 9 and more particularly between 4 and 8.

According to an alternative form of the invention, the composition contains:
from 0.1 to 20% and preferably from 0.1 to 10% of insoluble silicone;
from 8 to 30% of a detergent surface-active agent as defined above;
from 1 to 10% of ($C_7$-$C_{17}$)acylisethionate or of alkyl methyltaurate;
from 1 to 8% of ($C_2$-$C_4$)polyhydric alcohol myristate;
from 0.5 to 8% of alkanolamide alkyl ether or of $C_8$-$C_{16}$ fatty acid alkanolamide.

The aqueous medium may consist solely of water or a mixture of water and of a cosmetically acceptable solvent such as $C_1$-$C_4$ lower alcohols like ethanol, isopropanol, n-butanol, alkylene glycols like ethylene glycol, glycol ethers.

In addition to the combination defined according to the invention the compositions in accordance with the invention may contain viscosity-regulating agents such as electrolytes, hydrotropes or other thickeners.

Among these adjuvants there may be mentioned sodium chloride and sodium xylenesulphonate.

The viscosity-regulating agents are employed, according to the invention, in proportions which may go up to 10% relative to the total weight of the composition.

The compositions in accordance with the invention may also contain up to 3% of opalescent or opacifying agents such as sodium or potassium palmitates, sodium or potassium stearates or hydroxystearates and ethylene glycol mono- or distearate. glycol.[sic]

The compositions in accordance with the invention may also contain other agents whose effect is to improve the cosmetic properties of hair or of the skin without, however, impairing the stability of the compositions, such as cationic surface-active agents, anionic or nonionic or cationic or amphoteric polymers or optionally quaternised proteins.

These compositions may also contain various adjuvants usually employed in cosmetics, such as perfumes, colorants, preserving agents, sequestrants, foam stabilisers and acidifying or alkalifying agents which are well known in cosmetics.

The compositions according to the invention are preferably employed as shampoos for washing and conditioning hair and are applied, in this case, to wet or dry hair in quantities which are effective for washing it, this application being followed by a rinse.

The compositions in accordance with the invention can also be employed as shower gels for washing hair and the skin, in which case they are applied to wet skin and hair and are rinsed off after application.

The following examples are intended to illustrate the invention without, however, being limiting in nature.

EXAMPLE 1

| | |
|---|---|
| Sodium lauryl ether sulphate oxyethylenated with 2.2 moles of ethylene oxide | 11.2 g |
| Laurylbetaine | 2.4 g |
| Copra isopropanolamide | 4.0 g |
| Ethylene glycol dimyristate | 3.0 g |
| Polydimethylsiloxane sold under the name Silbione 700 47 V 500 000 oil by Rhone-Poulenc | 2.0 g |
| Perfume, preserving agents, q.s. | |
| Water q.s. | 100.0 g |

This composition is employed for washing hair and the skin and, after drying, endows hair with softness and sheen and allows good disentangling and leaves the skin soft.

EXAMPLE 2

| | |
|---|---|
| Sodium lauryl ether sulphate oxyethylenated with 2.2 moles of ethylene oxide | 8.4 g |
| Laurylbetaine | 6.0 g |
| Copra isopropanolamide | 0.5 g |
| Ethylene glycol dimyristate | 1.0 g |
| Polydimethylsiloxane sold under the name Silbione 700 47 V 300 oil by Rhone-Poulenc | 0.5 g |
| Perfume, preserving agents, q.s. | |
| Water q.s. | 100.0 g |

EXAMPLE 3

| | |
|---|---|
| Ammonium ($C_{12}$-$C_{14}$)alkyl sulphate | 7.5 g |
| Ammonium lauryl ether sulphate (3 EO) | 6.2 g |
| Sodium cocoylisethionate | 6.0 g |

-continued

| | |
|---|---|
| Laurylbetaine | 1.2 g |
| (C$_{13}$-C$_{15}$)Alkoxydiethoxymethylmonoethanolamide | 2.0 g |
| Polydimethylsiloxane (MW: 250 000 viscosity at 25° C.: 500 000 cSt) | 3.0 g |
| Stearyldimethylbenzylammonium chloride | 1.0 g |
| Hydroxypropyl guar gum quaternised with 2,3-epoxy-propyltrimethylammonium chloride | 0.15 g |
| Ethylene glycol dimyristate | 2.5 g |
| Sterilised demineralised water q.s. | 100.00 g |

EXAMPLE 4

| | |
|---|---|
| Sodium (C$_{12}$-C$_{14}$)alkyl ether sulphate (2.2 EO) | 14.0 g |
| Sodium cocoylisethionate | 6.0 g |
| Laurylbetaine | 2.4 g |
| Polydimethylsiloxane (MW: 250 000 viscosity at 25° C.: 500 000 cSt) | 3.0 g |
| Ethylene glycol dimyristate | 2.0 g |
| (C$_{13}$-C$_{15}$)Alkoxydiethoxymethylmonoethanolamide | 2.0 g |
| Sterilised demineralised water q.s. | 100.00 g |

The compositions of Examples 2 to 4 impart to hair and to the skin properties which are similar to those mentioned in the case of Example 1.

We claim:

1. Composition for washing and conditioning keratinous substances, in particular hair and the skin, characterised in that it contains in an aqueous medium
   at least one detergent surface-active agent,
   at least one insoluble silicone,
   at least one myristate of a C$_2$-C$_4$ polyhydric alcohol,
   at least one (C$_1$-C$_4$)alkanolamide alkyl ether and/or C$_8$-C$_{16}$ fatty acid (C$_1$-C$_4$) alkanolamide.

2. Composition according to claim 1, characterised in that it contains:
   from 5 to 50% by weight of at least one detergent surface-active agent,
   from 0.1 to 20% by weight of at least one insoluble silicone,
   from 1 to 8% by weight of myristate of a C$_2$-C$_4$ polyhydric alcohol, and
   from 0.5 to 8% by weight of alkanolamide alkyl ether and/or of C$_8$-C$_{16}$ fatty acid (C$_1$-C$_4$)alkanolamide.

3. Composition according to claim 1 characterised in that the detergent surface-active agents are chosen from anionic, amphoteric or zwitterionic or nonionic surface-active agents or their mixtures.

4. Composition according to claim 3 characterised in that the anionic surface-active agents are chosen from the alkali metal salts, the magnesium salts, the ammonium salts, the amine salts or the aminoalcohol salts of the following compounds:
   alkyl sulphates, alkyl ether sulphates, alkylamidoether sulphates, alkylaryl polyether sulphates and monoglyceride sulphates;
   alkylsulphonates, alkylamidesulphonates, alkylarylsulphonates, olefin sulphonates, paraffin sulphonates;
   alkylsulphosuccinates, alkyl ether sulphosuccinates, alkylamidesulphosuccinates;
   alkylsulphosuccinamates;
   alkylsulphoacetates;
   alkyl phosphates, alkyl ether phosphates;
   acylsarcosinates; the alkyl or acyl radical in these compounds consisting of a carbon chain containing 12 to 20 carbon atoms;
   fatty acid salts chosen from the salts of oleic, ricinoleic, palmitic and stearic acids; copra oil or hydrogenated copra oil acids, and acyllactylates in which the acyl radical contains from 8 to 20 carbon atoms;
   polyoxyalkylenated carboxylic ether acids of formula:

$$R-(OC_3H_6)_p-(OC_2H_4)_n-OCH_2COOA$$

in which R denotes an alkyl radical or a mixture of linear or branched, C$_8$-C$_{22}$ alkyl or alkenyl radicals, a (C$_8$-C$_9$)alkylphenyl radical, an R'CONH—CH$_2$—CH$_2$— group with R' denoting a C$_{11}$-C$_{21}$ linear or branched alkyl or alkenyl radical;
   n is an integer or decimal number between 2 and 24,
   p is an integer or decimal number between 0 and 6,
   A denotes a hydrogen atom or Na, K, Li, ½ Mg or a monoethanolamine, ammonium or triethanolamine residue.

5. Composition according to claim 1, characterised in that the surface-active agent is a nonionic surface-active agent chosen from:
   alcohols, alkylphenols and polyethoxylated, polypropoxylated or polyglycerolated fatty acids containing a linear fatty chain containing 8 to 18 carbon atoms, the number of ethylene oxide or propylene oxide groups being between 2 and 50 and the number of glycerol groups being between 2 and 30;
   copolymers of-propylene and ethylene oxide;
   condensates of propylene and ethylene oxide with fatty alcohols;
   polyethoxylated fatty amides;
   polyglycerolated fatty amides;
   polyethoxylated fatty amines;
   oxyethylenated sorbitan fatty acid esters;
   sucrose fatty acid esters;
   polyethylene glycol fatty acid esters;
   phosphoric triesters;
   amine oxides.

6. Composition according to claim 3, characterised in that the amphoteric or zwitterionic surface-active agents are chosen from:
   derivatives of aliphatic secondary or tertiary amines in which the aliphatic radical is a linear or branched chain containing 8 to 18 carbon atoms and which contains at least one carboxylic, sulphonate, sulphate, phosphate or phosphonate hydrosolubilising anionic group;
   (C$_8$-C$_{20}$) alkylbetaines, (C$_8$-C$_{20}$) alkylsulphobetaines, (C$_8$-C$_{20}$)alkylamido(C$_1$-C$_6$)alkylbetaines or (C$_8$-C$_{20}$)alkylamido(C$_1$-C$_6$)alkylsulphobetaines.

7. Composition according to claim 1 characterised in that mixtures of detergent surface-active agents and in particular mixtures of anionic surface-active agents and of amphoteric, zwitterionic or nonionic surface-active agents are employed.

8. Composition according to claim 1 characterised in that the silicone is chosen from polyorganosiloxanes which are insoluble in aqueous media, which are in the form of oils, waxes, gums or resins.

9. Composition according to claim 1, characterised in that the si a nonvolatile silicone chosen from polyalkylsiloxanes, polyarylsiloxanes, polyalkylarylsiloxanes, silicone gums and resins, organomodified polysiloxanes and mixtures thereof.

10. Composition according to claim 9, characterised in that the nonvolatile silicone is chosen from:
    linear polydimethylsiloxanes containing trimethylsilyl end groups, linear polydimethylsiloxanes containing dimethylsilanol end groups, poly($C_1$-$C_{20}$)alkylsiloxanes containing at least one $C_1$-$C_{20}$ fatty chain, linear and/or branched polydimethylmethylphenylsiloxanes and polydimethyldiphenylsiloxanes, silicone gums of molecular mass of between 200,000 and 1,000,000, employed by themselves or in the form of mixtures in a solvent, organopolysiloxane resins consisting of crosslinked siloxane systems containing the units $R_2SiO_{2/2}$, $RSiO_{3/2}$ and $SiO_{4/2}$, in which R denotes a hydrocarbon group containing from 1 to 6 carbon atoms or a phenyl group;

organomodified silicones chosen from silicones containing in their structure one or more organofunctional groups attached directly to the siloxane chain or attached by means of a hydrocarbon radical.

11. Composition according to claim 10, characterised in that the silicone gums are chosen from the group consisting of the following copolymers:
poly/(dimethylsiloxane)/(methylvinylsiloxane)/,
poly/(dimethylsiloxane)/(diphenylsiloxane)/,
poly/(dimethylsiloxane)/(phenylmethylsiloxane)/,
poly/(dimethylsiloxane)/(diphenylsiloxane)/(methylvinylsiloxane)/;
and the following mixtures:
the mixtures made up of a polydimethylsiloxane hydroxylated at a chain end and of a cyclic polydimethylsiloxane;
the mixtures made up of a polydimethylsiloxane gum and of a cyclic silicone;
mixtures of two polydimethylsiloxanes of different viscosities.

12. Composition according to claim 10, characterised in that the organomodified silicones are chosen from polyorganosiloxanes containing:
a) polyethyleneoxy and/or polypropyleneoxy groups, optionally containing alkyl groups;
b) substituted or unsubstituted amine groups;
c) thiol groups;
d) carboxylate groups;
e) alkoxylated groups;
f) hydroxyalkyl groups corresponding to the following formula:

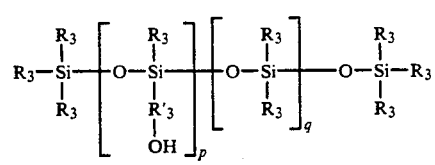

(I)

in which:
the radicals $R_3$, which are identical or different, are chosen from methyl and phenyl radicals, at least 60 mol % of the radicals $R_3$ being methyl;
the radical $R'_3$ is a $C_2$-$C_{18}$ divalent hydrocarbon alkylene chain unit;
p is between 1 and 30 inclusive;
q is between 1 and 150 inclusive.
g) acyloxyalkyl groups corresponding to the following formula:

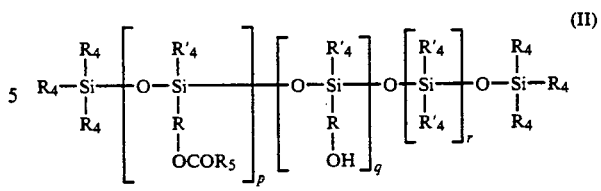

(II)

in which:
$R_4$ denotes methyl, phenyl, —OCOR″, hydroxyl, where only one $R_4$ per silicon atom may be OH;
$R'_4$ denotes methyl or phenyl, at least 60 mol % of the total of the radicals $R_4$ and $R'_4$ is methyl;
$R_5$ denotes $C_8$-$C_{20}$ alkyl or alkenyl;
R denotes a $C_2$-$C_{18}$ linear or branched divalent hydrocarbon alkylene;
r is between 1 and 120 inclusive;
p is between 1 and 30;
q is equal to 0 or is smaller than 0.5 p, the sum p+q being between 1 and 30; it being possible for the polyorganosiloxanes of formula (II) to contain

groups, in proportions not exceeding 15% of the sum p+q+r;
h) alkylcarboxylic groups;
i) 2-hydroxyalkylsulphonate groups;
j) 2-hydroxyalkylthiosulphate groups;
k) hydroxyacylamino groups 13. Composition according to claim 1 characterised in that the silicone is a volatile silicone which has a boiling point of between 60° and 260° C.

14. Composition according to claim 13, characterised in that the volatile silicone is chosen from cyclic silicones with 3 to 7 and preferably 4 to 5 carbon atoms and their mixtures with organic compounds derived from silicon, or cyclocopolymers from the class of dimethylsiloxane/methylalkylsiloxanes, the linear silicones containing from 2 to 9 silicon atoms.

15. Composition according to claim 1 characterised in that the polyhydric alcohol myristate is an ethylene glycol, propylene glycol or glycerol myristate.

16. Composition according to claim 15, characterised in that ethylene glycol dimyristate containing at least 95% of $C_{14}$ radicals is employed.

17. Composition according to claim 1 characterised in that the alkanolamide alkyl ether is ($C_{13}$-$C_{15}$) alkoxydiethoxymethylmonoethanolamide.

18. Composition according to claim 1 characterised in that the $C_8$-$C_{16}$ fatty acid alkanolamide is chosen from copra diethanolamide, copra monoethanolamide or copra monoisopropanolamide.

19. Composition for washing and conditioning keratinous substances, characterised in that it contains in an aqueous medium:
from 8 to 30% of a detergent surface-active agent;
from 1 to 10% and in particular from 1 to 4% of an insoluble silicone;
from 1.5 to 5% of myristate of a $C_2$-$C_4$ polyhydric alcohol;
from 0.5 to 8% of an amide chosen from ($C_1$-$C_4$)alkanolamide alkyl ether, the alkyl radical containing 13 to 15 carbon atoms and $C_8-C_{16}$ fatty acid $(C_1-C_4)$alkanolamides.

20. Composition for washing and conditioning keratinous substances, characterised in that it contains in an aqueous medium:
   from 0.1 to 20% by weight of an insoluble silicone;
   from 8 to 30% by weight of a detergent surface-active agent;
   from 0.1 to 20% of insoluble silicone;
   from 1 to 10% by weight of $(C_7-C_{17})$acylisethionate or of alkyl methyltaurate;
   from 1 to 8% by weight of $C_2-C_4$ polyhydric alcohol myristate;
   from 0.5 to 8% by weight of alkanolamide alkyl ether or of $C_8-C_{16}$ fatty acid alkanolamide.

21. Composition according to claim 1, characterised in that the pH of the compositions is between 3 and 9 and preferably between 4 and 8.

22. Composition according to claim 1, characterised in that it additionally contains a viscosity-regulating agent chosen from electrolytes, hydrotropes and other thickeners which may be present as up to 10% by weight relative to the total weight of the composition, opalescent or opacifying agents chosen from sodium or magnesium palmitates and ethylene glycol mono- or distearates; cationic surface-active agents, anionic, nonionic, cationic or amphoteric polymers or optionally quaternised proteins and mixtures thereof.

23. Use as a shampoo of the composition as defined in claim 1.

24. Use as a shower gel of the composition defined in claim 1.

25. Process for washing and conditioning hair, characterized in that at least one composition as defined in claim 1 is applied to hair and that after a period of exposure, rinsing and optionally a second washing is carried out.

* * * * *